US009829546B2

United States Patent
Yu et al.

(10) Patent No.: US 9,829,546 B2
(45) Date of Patent: Nov. 28, 2017

(54) LOW-TEMPERATURE COOLING APPARATUS AND SUPERCONDUCTING QUANTUM INTERFERENCE DEVICE SENSOR MODULE

(71) Applicant: Korea Research Institute of Standards and Science, Daejeon (KR)

(72) Inventors: Kwon-Kyu Yu, Daejeon (KR); Yong-Ho Lee, Daejeon (KR); Hyukchan Kwon, Daejeon (KR); Jin-Mok Kim, Daejeon (KR); Kiwoong Kim, Daejeon (KR); Sang-Kil Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 287 days.

(21) Appl. No.: 14/692,294

(22) Filed: Apr. 21, 2015

(65) Prior Publication Data

US 2015/0226813 A1    Aug. 13, 2015

Related U.S. Application Data

(63) Continuation of application No. PCT/KR2013/009107, filed on Oct. 11, 2013.

(30) Foreign Application Priority Data

Oct. 29, 2012 (KR) .................. 10-2012-0120380

(51) Int. Cl.
*H05K 7/02* (2006.01)
*G01R 33/035* (2006.01)
(Continued)

(52) U.S. Cl.
CPC ............ *G01R 33/0354* (2013.01); *A61B 5/05* (2013.01); *G01R 33/0047* (2013.01);
(Continued)

(58) Field of Classification Search
None
See application file for complete search history.

(56) References Cited

U.S. PATENT DOCUMENTS 4,761,611 A * 8/1988 Hoenig .............. G01R 33/0358
324/248
5,065,582 A * 11/1991 Seifert .............. G01R 33/0354
335/216
(Continued)

FOREIGN PATENT DOCUMENTS

| JP | 09166654 A | 12/1995 |
|---|---|---|
| JP | 11097754 A | 9/1997 |
| JP | 2001/124837 A | 10/1999 |

*Primary Examiner* — Courtney Smith
(74) *Attorney, Agent, or Firm* — Jenkins, Wilson, Taylor & Hunt, P.A.

(57) ABSTRACT

Provided are a low-temperature cooling apparatus and a superconducting quantum interference device (SQUID) sensor module. The low-temperature cooling apparatus includes an outer container; an inner container disposed inside the outer container, the inner container including a neck portion having a first diameter and a body portion having a second diameter greater than the first diameter; an insert inserted into the neck portion of the inner container; and a plurality of SQUID sensor modules inserted into the body portion of the inner container. Each of the SQUID sensor modules is in the form of a fan-shaped pillar and is fixedly coupled with an inner bottom plate of the inner container.

16 Claims, 10 Drawing Sheets

(51) Int. Cl.
   *A61B 5/05*       (2006.01)
   *G01R 33/00*      (2006.01)
   *A61B 5/04*       (2006.01)
(52) U.S. Cl.
   CPC ........... *G01R 33/0082* (2013.01); *H05K 7/02*
                   (2013.01); *A61B 5/04005* (2013.01)

(56) References Cited

U.S. PATENT DOCUMENTS

| | | | | |
|---|---|---|---|---|
| 5,218,297 A | * | 6/1993 | Nakane | G01R 33/0358 |
| | | | | 324/248 |
| 5,319,307 A | * | 6/1994 | Simmonds | G01R 33/0358 |
| | | | | 257/31 |
| 5,438,036 A | * | 8/1995 | Matsuura | G01R 33/0358 |
| | | | | 257/33 |
| 5,825,183 A | * | 10/1998 | Morooka | G01R 33/022 |
| | | | | 324/241 |
| 6,285,186 B1 | * | 9/2001 | Morooka | G01R 33/0354 |
| | | | | 324/248 |
| 6,563,312 B2 | * | 5/2003 | Saho | F17C 3/085 |
| | | | | 324/248 |

* cited by examiner

LOW-TEMPERATURE COOLING APPARATUS AND SUPERCONDUCTING QUANTUM INTERFERENCE DEVICE SENSOR MODULE

CROSS-REFERENCE TO RELATED APPLICATION

This application is a continuation of and claims priority to PCT/KR2013/009107 filed on Oct. 11, 2013, which claims priority to Korea Patent Application No. 10-2012-0120380 filed on Oct. 29, 2012, the entirety of which is hereby incorporated by reference herein.

BACKGROUND

1. Technical

The present disclosure relates generally to cooling apparatuses and, more particularly, to a split-type low-temperature cooling apparatus.

2. Description of the Related Art

A superconducting quantum interference device (hereinafter referred to as "SQUID") sensor used to measure biomagnetism operates at extremely low temperature of absolute temperature 4K. The SQUID sensor has measurement sensitivity of several to tens of $fT/\sqrt{Hz}$. Accordingly, a SQUID system for measuring biomagnetism requires a low-temperature coolant storage container capable of storing an ultralow-temperature coolant. The low-temperature coolant storage container must be formed of a non-magnetic material to stably operate a SQUID sensor without distortion of a magnetic field generated from a living body. Moreover, liquid helium used as a coolant of the SQUID sensor is high-priced. Accordingly, since the supply of a coolant is limited, an evaporation rate of the coolant needs to be minimized.

SUMMARY

Embodiments of the present disclosure provide a low-temperature cooling apparatus having a structure to reduce vibration noise and an evaporation rate of a coolant and a SQUID sensor module mounted on the low-temperature cooling apparatus.

A low-temperature cooling apparatus according to an embodiment of the present disclosure may include an outer container; an inner container disposed inside the outer container, the inner container including a neck portion having a first diameter and a body portion having a second diameter greater than the first diameter; an insert inserted into the neck portion of the inner container; and a plurality of SQUID sensor modules inserted into the body portion of the inner container. Each of the SQUID sensor modules may be in the form of a fan-shaped pillar and be fixedly coupled with an inner bottom plate of the inner container.

In an example embodiment, the inner bottom plate may include a partition such that the SQUID sensor module is inserted and aligned with the inner bottom plate.

In an example embodiment, the insert may further include an intermediate connection block. An interconnection of the SQUID sensor module may be electrically connected to the intermediate connection block.

In an example embodiment, the SQUID sensor module may include an upper sensor coupling plate having a through-hole; a lower sensor coupling plate including a protrusion disposed to be aligned with the through-hole; an upper printed circuit board disposed below the upper sensor coupling plate, the upper printed circuit board having a printed circuit board through-hole aligned with the through-hole; and a SQUID sensor having one end inserted into the through-hole and the printed circuit board through-hole and the other end having a groove inserted into the protrusion.

In an example embodiment, the upper sensor coupling plate may further have an auxiliary through-hole.

In an example embodiment, the upper sensor coupling plate may further have a trench formed on its bottom surface.

In an example embodiment, the SQUID sensor module may further include a module coupling pillar coupled with the inner bottom plate through a fan-shaped central region.

In an example embodiment, the SQUID sensor may include a bobbin on which a pick-up coil is wound; a SQUID mounted on the bobbin and electrically connected to the pick-up coil; and a printed circuit board electrically connected to the SQUID and fixed to the bobbin.

In an example embodiment, the bobbin may include a cylindrical body portion; a cut-out portion connected to the body portion and cut out such that its side surface forms a plane; a square-pillar portion connected to the cut-out portion, the square-pillar portion having a square section; and a cylindrical portion extending from the center of the square-pillar portion. The groove may be formed on a bottom surface of the body portion.

In an example embodiment, each of the SQUID sensor modules may include a manganin wire electrically connected to the SQUID sensor module; a plastic braided wire to protect the manganin wire; and a connection connector connected to the managing wire.

A low-temperature cooling apparatus according to another embodiment of the present disclosure may include an outer container; an inner container disposed inside the outer container, the inner container including a neck portion having a first diameter and a body portion having a second diameter greater than the first diameter; an insert inserted into the neck portion of the inner container; and a plurality of SQUID sensor modules inserted into the body portion of the inner container. Each of the SQUID sensor modules may be aligned and fixedly coupled with an inner bottom plate of the inner container isolated by a partition.

A SQUID sensor module inserted into a low-temperature cooling apparatus including an inner container and an outer container according to an embodiment of the present disclosure may include an upper sensor coupling plate having a coupling groove and a through-hole through which a coupling tool is coupled; a lower sensor coupling plate including a protrusion disposed to be aligned with the through-hole; an upper printed circuit board disposed below the upper sensor coupling plate, the upper printed circuit board having a printed circuit board through-hole aligned with the through-hole; and a SQUID sensor having one end inserted into the through-hole and the printed circuit board through-hole and the other end having a groove inserted into the protrusion.

In an example embodiment, the upper sensor coupling plate may further have an auxiliary through-hole through which coolant bubbles pass.

In an example embodiment, the upper sensor coupling plate may further have a trench formed on its bottom surface. Interconnections of the SQUID sensor module may be buried in the trench.

In an example embodiment, the SQUID sensor module may further include a module coupling pillar coupled with a bottom plate of the inner container through the SQUID sensor module.

In an example embodiment, the SQUID sensor may include a bobbin on which a pick-up coil is wound; a SQUID mounted on the bobbin and electrically connected to the pick-up coil; and a printed circuit board electrically connected to the SQUID and fixed to the bobbin.

In an example embodiment, the bobbin may include a cylindrical body portion; a cut-out portion connected to the body portion and cut out such that its side surface forms a plane; a square-pillar portion connected to the cut-out portion, the square-pillar portion having a square section; and a cylindrical portion extending from the center of the square-pillar portion. The groove may be formed on a bottom surface of the body portion.

In an example embodiment, the SQUID sensor module may further include a manganin wire electrically connected to the SQUID sensor module; a plastic braided wire to protect the manganin wire; and a connection connector connected to the managing wire.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
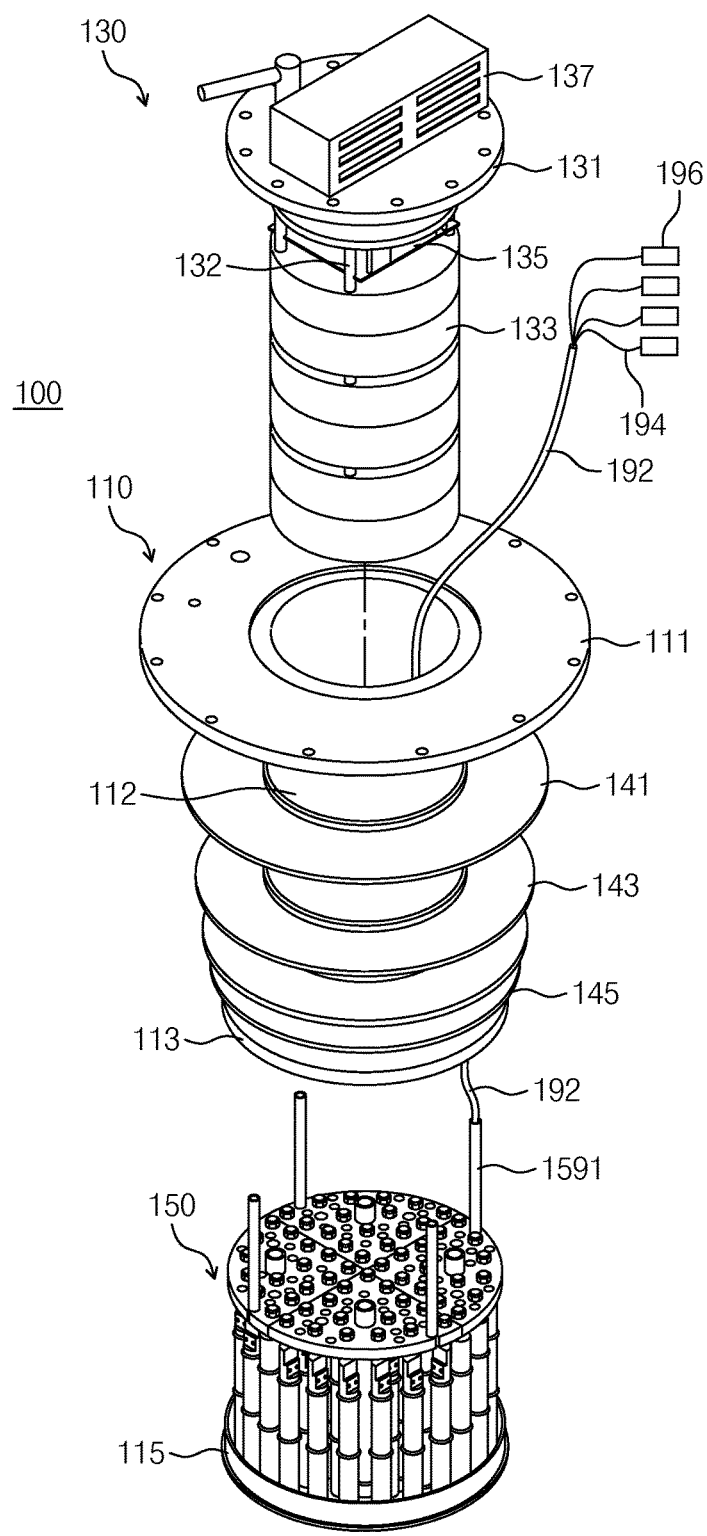
FIG. 1 is a partial perspective view of a low-temperature cooling apparatus according to an embodiment of the present disclosure.
Figure 2:
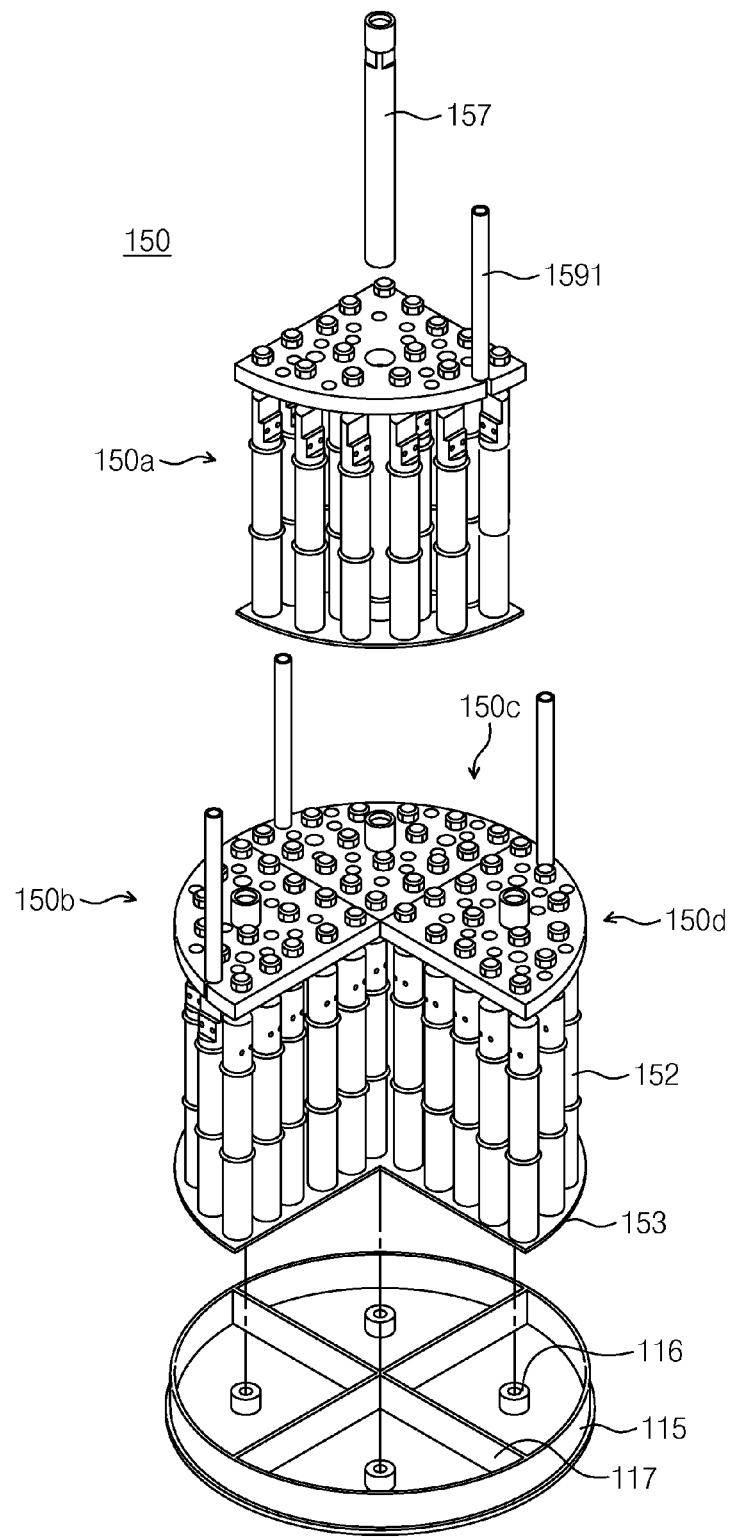
FIG. 2 is a perspective view of a SQUID sensor module in FIG. 1.
Figure 3:
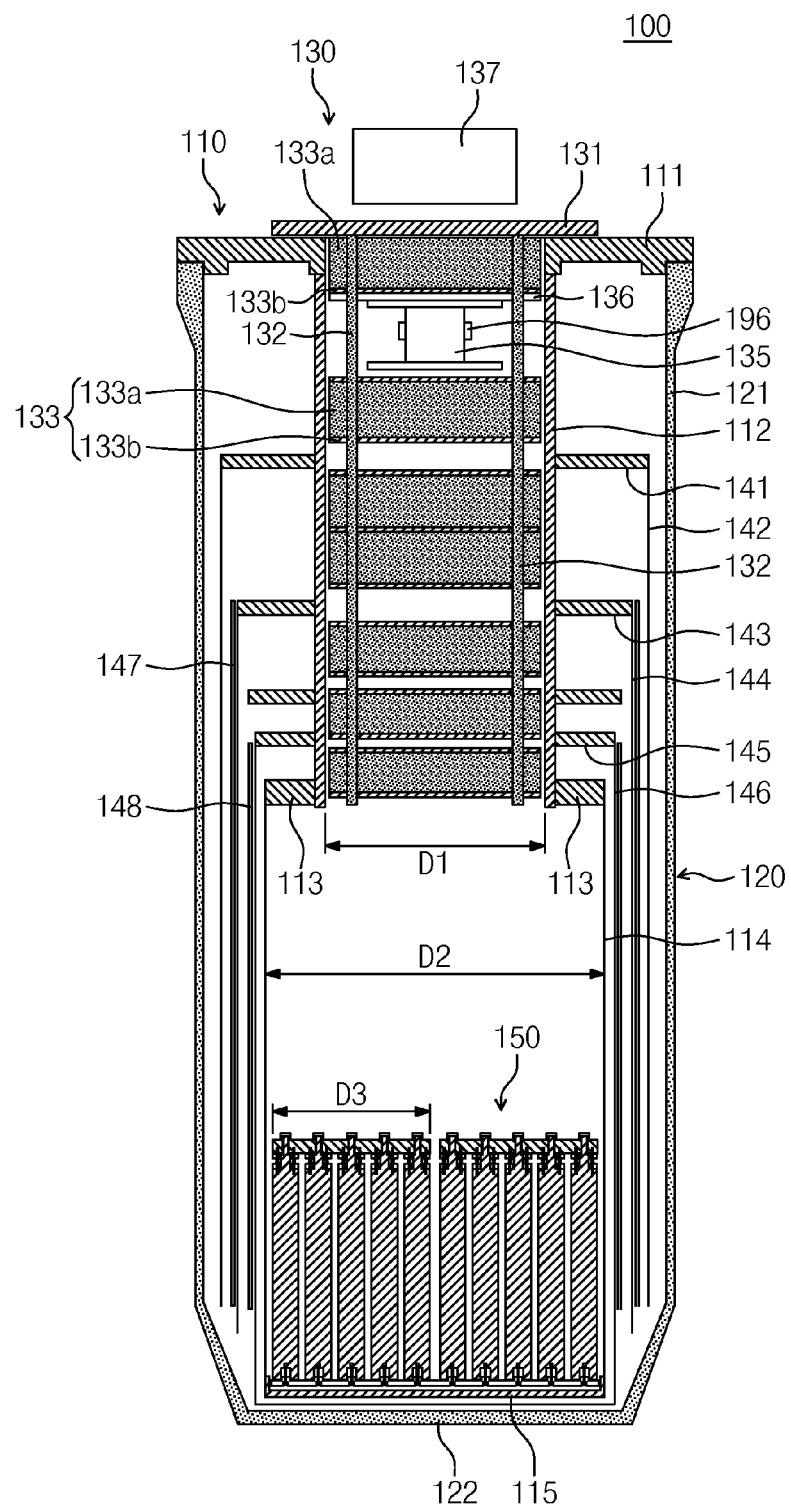
FIG. 3 is a cross-sectional view of the low-temperature cooling apparatus in FIG. 1.
Figure 4:
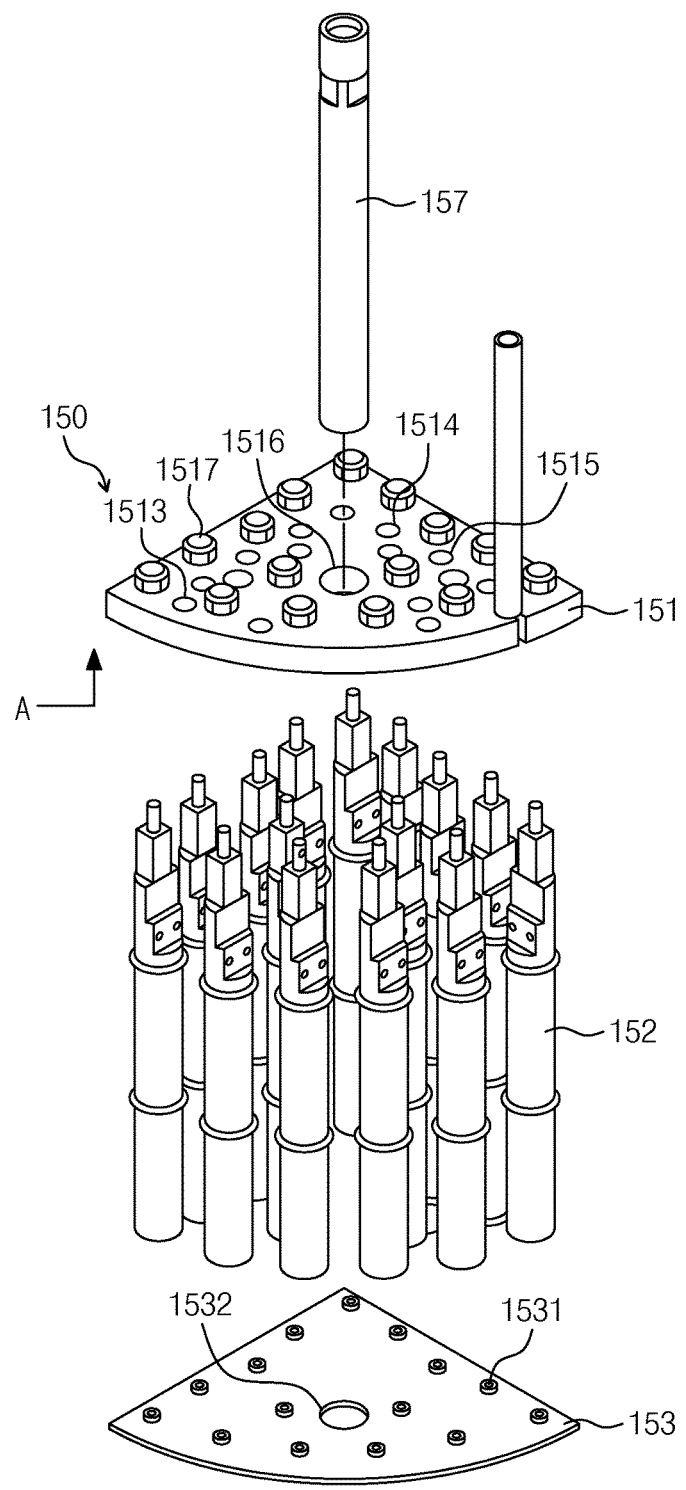
FIG. 4 is a perspective view of a SQUID sensor module.
Figure 5:
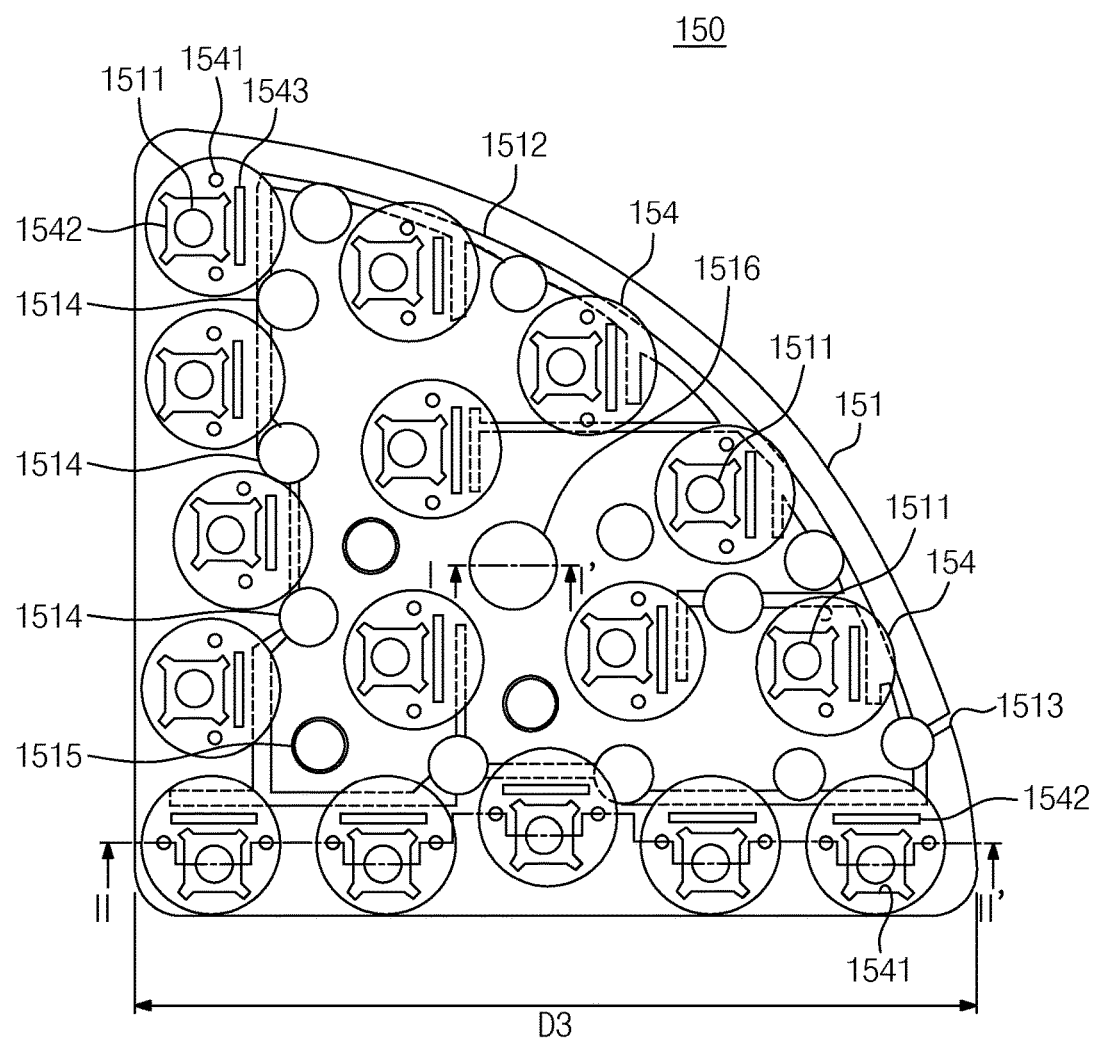
FIG. 5 is a top plan view of an upper sensor coupling plate when viewed in an A direction in FIG. 4.
Figure 6:
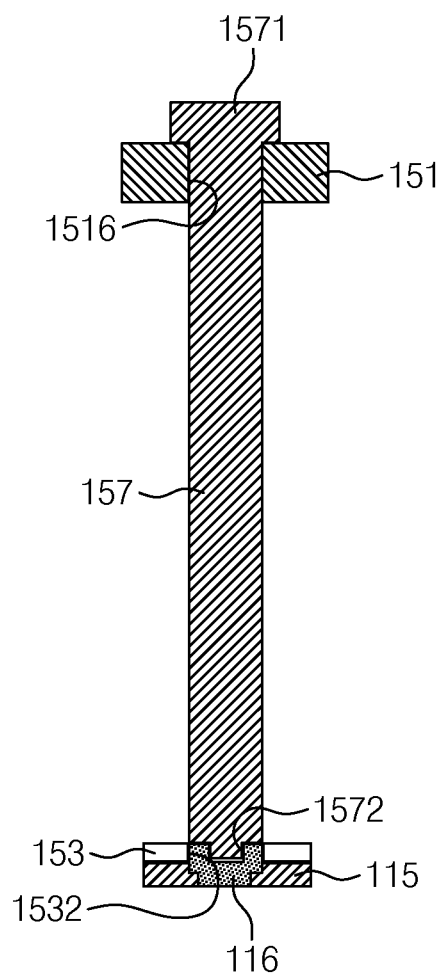
FIG. 6 is a cross-sectional view taken along the line I-I' in FIG. 5.
Figure 7:
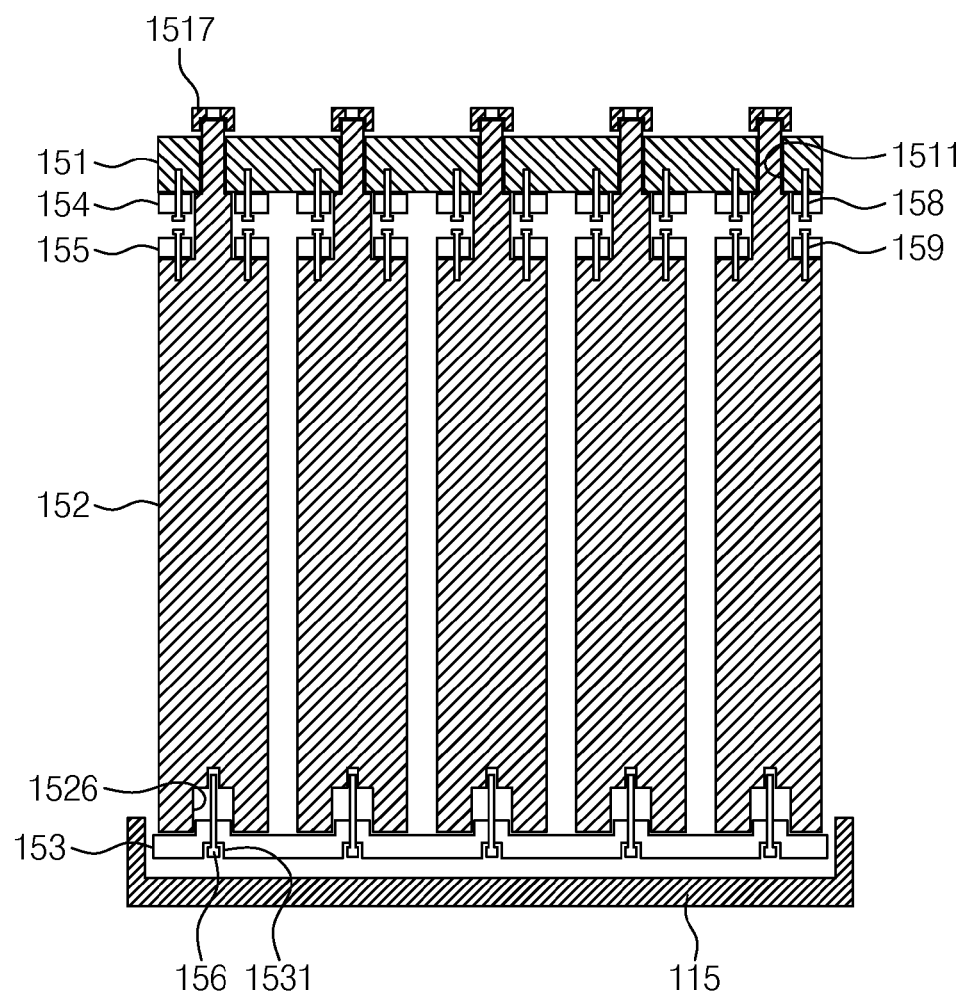
FIG. 7 is a cross-sectional view taken along the line II-II' in FIG. 5.
Figure 8A:
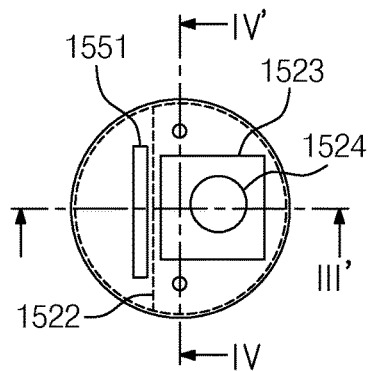
FIG. 8A is a top plan view of a SQUID sensor.
Figure 8B:
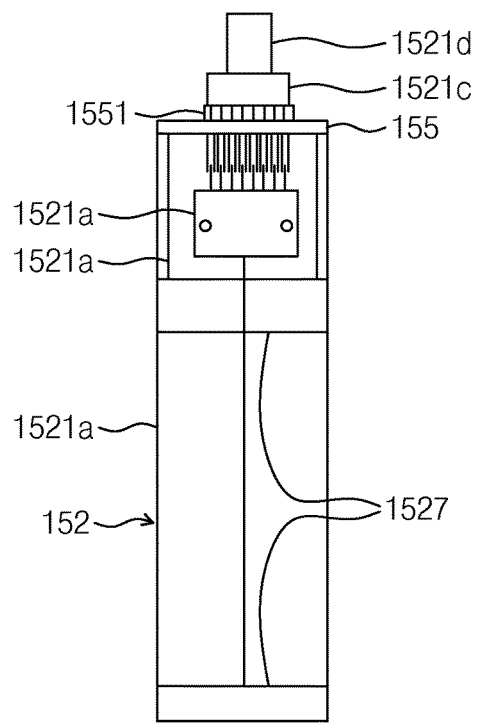
FIG. 8B is a front view of a SQUID sensor.
Figure 8C:
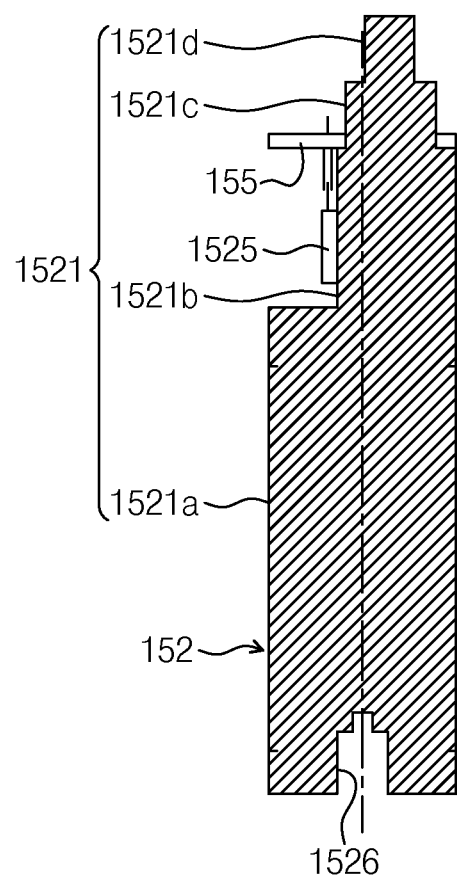
FIG. 8C is a cross-sectional view taken along the line III-III' in FIG. 8A.
Figure 8D:
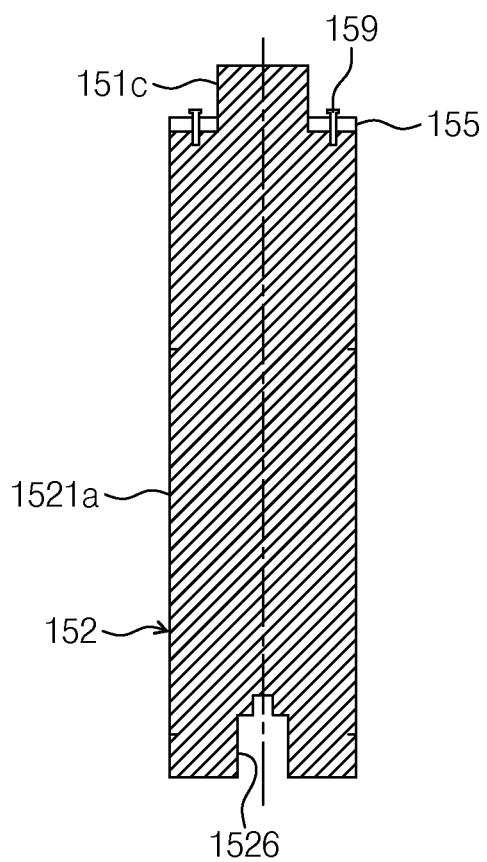
FIG. 8D is a cross-sectional view taken along the line IV-IV' in FIG. 8A.

A low-temperature cooling container includes an outer container and an inner container inserted into the outer container. A space between the inner container and the outer container is maintained at a vacuum state. In general, a structure of the low-temperature coolant storage container for reducing a liquid helium evaporation rate uses a three-fold thermal shield to reduce a temperature gradient. Thirty sheets of superinsulator and thirty sheets of polyester net, total 100 folds or more are mounted between respective thermal shields to block radiant heat influx.

A vacuum layer is disposed to prevent heat conduction to the outside from a main reservoir to store a low-temperature coolant. A size and a shape of a low-temperature coolant storage container vary depending on a biomagnetism measurement part (e.g., brain, heart, liver, electromyogram, etc.). A coolant evaporation rate is greatly affected by the size and the shape of the low-temperature coolant storage container.

In general, a SQUID apparatus for measuring biomagnetism simultaneously obtains signals generated in a large area such as heart and head and analyzes the obtained signals. Accordingly, a SQUID system for measuring biomagnetism uses a multi-channel SQUID sensor. Conventionally, 64 channels are used in case of magnetocardiography (MCG) and 128 to 300 channels are used in case of magnetoencephalography (MEG).

A measurement probe is for coupling a multi-channel SQUID sensor. In a conventional measurement probe, a plurality of SQUID sensors are mounted on a circular plate for coupling a sensor. An insert is disposed at a neck portion of the inner container. The insert is fixedly coupled with the measurement probe, and the measurement probe is dipped in a coolant.

Conventionally, a material of the low-temperature coolant storage container is G-10 epoxy that is a glass reinforced epoxy. The G-10 epoxy has low thermal conductivity and shrinkage. However, when G-10 epoxy produced by a winding technique is cooled from room temperature (absolute temperature 300K) to liquid helium temperature (4K), shrinkage of several millimeters (mm) per meter (m) occurs. Accordingly, the measurement probe requires a shock absorber such as a spring for lengthwise arrangement of a low-temperature coolant storage container for cooling the measurement probe. The shock absorber may be implemented within the insert.

The heat influx from the low-temperature coolant storage container to a low-temperature coolant is performed by radiant heat and conduction heat. Due to a structure of the low-temperature coolant storage container, the heat influx caused by the conduction heat is limited on a side surface and a bottom of the container by a vacuum layer. However, most of the heat influx caused by the radiant heat may be blocked by mounting a multi-layered structure including a superinsulator and a polyester net.

The heat influx caused by the conduction heat is performed mainly through G-10 epoxy constituting a measurement probe and an inlet of the low-temperature coolant storage container for inserting the measurement probe. A multi-channel SQUID for measuring biomagnetism requires a large-area measurement probe. The measurement probe is inserted via the inlet of the low-temperature coolant storage container. Therefore, an inlet of a low-temperature coolant storage container for cooling the measurement probe needs to be large enough to insert the measurement probe. An evaporation rate of a coolant increases in proportion to a sectional area of the inlet of the low-temperature coolant storage container. A structure for reducing the inlet of the low-temperature coolant storage container is required to reduce loss of the coolant.

In a conventional SQUID for measuring biomagnetism, a measurement probe supports a SQUID sensor coupling circular plate by using a plurality of epoxy tubes extending from a top plate of an inner container. A shock absorber is required for lengthwise arrangement of the measurement probe and the low-temperature coolant storage container. In this case, the measurement probe on which the low-temperature coolant storage container and a SQUID sensor are mounted is placed on the bottom of the container inside the container while not being fixed. The shock absorber causes external vibration and internal vibration arising from bubbles generated in a coolant. Thus, the external vibration and the internal vibration cause vibration noise under a magnetic field. The vibration noise prevents the SQUID sensor from operating stably. When a fine biomagnetic signal is measured, the vibration noise may reduce a signal-to-noise ratio.

When SQUID gradiometers each having baseline length of tens of millimeters (mm) are fixed to a sensor coupling plate as multi-channels, lengths and directions of the SQUID gradiometers are not constant. Due to inconsistent sensor lengths, the SQUID gradiometers vibrate individually. The SQUID gradiometers measure signals including individually introduced vibration noises, respectively. Thus, accuracy of single analysis is reduced. If a pick-up coil direction of an individual sensor in a multi-channel SQUID system is not constant, the sensor measures another component with respect to a magnetic field generated from a signal source. As a result, an error of signal source localization may occur.

Preferred embodiments of the present disclosure will be described below in more detail with reference to the accompanying drawings. The present disclosure may, however, be embodied in different forms and should not be constructed as limited to the embodiments set forth herein. Rather, these embodiments are provided so that this disclosure will be thorough and complete, and will fully convey the scope of the present disclosure to those skilled in the art. Like numbers refer to like elements throughout.

A low-temperature cooling apparatus 100 according to an embodiment of the present disclosure includes an outer container 120, an inner container that is disposed inside the outer container 120 and includes including a neck portion 112 having a first diameter D1 and a body portion 114 having a second diameter D2 greater than the first diameter DE an insert 130 inserted into the neck portion 112 of the inner container 110, and a plurality of SQUID sensor modules 150 inserted into the body portion 114 of the inner container 110. Each of the SQUID sensor modules 150 is in the form of a fan-shaped pillar and is fixedly coupled with an inner bottom plate 115 of the inner container 150.

The outer container 120 includes an outer cylinder 121 including an outer bottom plate 112. The outer container 120 may be formed of G-10 epoxy. A lower portion of the outer container 120 may be tapered.

The inner container 110 includes a top plate, a neck portion 112 extending vertically from the top plate 111, an intermediate plate 113 connected to the neck portion 112, an inner body portion 114 extending vertically from the intermediate plate 113, and an inner bottom plate 115 to form a bottom surface of the inner body portion 114. The inner container 110 may be formed of G-10 epoxy, and a coupling portion may be coupled using an epoxy resin. The inner body portion 114 may store a coolant.

A washer-type first support 141 may be disposed on an outer side surface of the neck portion. A first thermal shield 142 may be coupled with an outer circumferential surface of the first support 141. A first thermal shield 142 may be formed of a cylindrical conductor. A lower portion of the first thermal shield 142 may have a slit shape. The first thermal shield 142 may extend in a vertical direction to cover the inner body portion 114.

A second support 143 may be vertically spaced apart from the first support 141 to be disposed on an outer side surface of the neck portion 112. The second support 142 may be in the form of a washer. A second thermal shield 144 may be formed of a cylindrical conductor. The second thermal shield 144 may be coupled with an outer circumferential surface of the second support 143. A diameter of the second thermal shield 144 may be smaller than that of the first thermal shield 142.

A third support 145 may be vertically spaced apart from the second support 143 to be coupled with an outer side surface of the neck portion 112. The third support 145 may be in the form of a washer. A third thermal shield 146 may be formed of a cylindrical conductor. The third thermal shield 146 may be coupled with an outer circumferential surface of the third support 145. A diameter of the third thermal shield 146 may be smaller than that of the second thermal shield 144. The third thermal shield 146 may extend to cover a bottom surface of the inner container 110.

A space between the inner container 110 and the outer container 120 may be in a vacuum state. A first superinsulation layer 147 may be disposed between the first thermal shield 142 and the second thermal shield 144. A second superinsulation layer 148 may be disposed between the second thermal shield 144 and the third thermal shield 146. A vacuum layer may blocks influx of conduction heat, and the first to third thermal shields 142, 144, and 146 may block influx of radiant heat. The first and second superinsulation layers 147 and 148 may block influx of radiant heat. The first and second superinsulation layers 147 and 148 may include thirty sheets of superinsulator and thirty sheets of polyester net, total 100 folds or more of superinsulator and polyester net.

The insert 130 may include an insert top plate 131, a guide rod 132 that is coupled with the insert top plate 131 and extends vertically, an insert baffle 133 inserted into the guide rod 132, and an intermediate connection block 135 disposed between insert baffles 133.

The insert top plate 131 may be in the form of a disc and be formed of G-10 epoxy. The guide rod 132 may be formed of G-10 epoxy and be in the form of a rod or a pipe. The insert baffle 133 may include a styrofoam 113a with superior warmth retention and a conductive plate 113b. The conductive plate 133b may include an aluminum-coated Mylar and a copper layer that are sequentially stacked to block radiant heat. The insert baffle 133 may block external heat conduction and radiant heat influx.

An upper connection block 137 may be disposed on the insert top plate 131 to connect the insert top plate 131 to a flux-locked-loop (FLL) circuit.

A styrofoam 133a may be disposed directly below the insert top plate 131, and a conductive plate 133b may be disposed below the styrofoam 133a. An auxiliary support plate 136a may be disposed below the conductive plate 133b to fix the intermediate connection block 135. The auxiliary support plate 136 may be formed of G-10 epoxy. The auxiliary support plate 136 may be inserted into the guide rod 132 to be fixed.

The intermediate connection block 135 may be connected to a 32-pin connector 196 electrically connected to an interconnection of the SQUID sensor module 150. The intermediate connection block 135 may be for connecting the 32-pin connector 196 connected to the interconnection of the SQUID sensor module 150. The intermediate connection block 135 may be electrically connected to the upper connection block 137 via a manganin wire. The intermediate connection block 135 is used for electric connection while blocking external mechanical connection.

Conventionally, a measurement probe includes a disc-shaped sensor coupling plate on which SQUID sensors are arranged. However, a diameter of a large-area sensor coupling plate cannot be greater than that of a neck portion. Therefore, the neck portion is formed to have a greater diameter than the sensor coupling plate. A heat influx rate from a coolant is in inverse proportion to length (L) of the neck portion of an inner container and increases in proportion to a sectional area of the neck portion.

According to an embodiment of the present disclosure, a sensor coupling plate for fixing a SQUID sensor may be divided into three, four or six parts to have a fan shape according to a size and a shape of the neck portion.

More specifically, when a sensor coupling plate is divided into four parts to have a fan shape, sixteen SQUID sensors may constitute a single SQUID sensor module. In this case, a sectional area of the neck portion when the sensor coupling plate is divided may be reduced more than twice when a disc-shaped plate is used. Thus, heat flowing through the neck portion may be reduced more than twice.

An inner bottom plate of the inner container is divided into four parts in the form of a fan to mutually fix the divided SQUID sensor module. In addition, a fixing nut is provided on the inner bottom plate to fix the SQUID sensor module.

Since each SQUID sensor module must have a position coordinate to localize a biomagnetic signal source and analyze a signal, the SQUID sensor module requires position alignment with the inner container. Accordingly, for the alignment of each SQUID sensor module with the inner container, the inner bottom plate may include a partition to guide each SQUID sensor module.

Since a conventional disc-shaped sensor coupling plate needs a large-area bottom surface of an inner container, the bottom surface is deformed by vacuum and cooling. For this reason, the bottom surface of the inner container may use a thick plate. Thus, a distance between a magnetic signal source generated at a measurement target and a pick-up coil of a SQUID sensor increases to cause signal attenuation.

According to the present disclosure, if a sensor coupling plate is divided into four or six parts, a bottom surface of an inner container having a thick partition to guide each SQUID sensor module may be provided. Thus, thickness of the bottom surface of the inner container may be reduced to decrease a distance between a magnetic signal source generated at a measurement target and a pick-up coil of a SQUID sensor.

The SQUID sensor module 150 includes an upper sensor coupling plate 151 having a through-hole 1511, a lower sensor coupling plate 153 including a protrusion 1531 disposed to be aligned with the through-hole 1511, an upper printed circuit board 154 which has a printed circuit board through-hole 1541 aligned with the through-hole 1511 and is disposed below the upper sensor coupling plate 151, and a SQUID sensor 152 having one end inserted into the through-hole 1511 and the printed circuit board through-hole 1541 and the other end having a groove 1526. The groove 1526 is disposed on the protrusion 1531

The upper sensor coupling plate 151 may have a fan shape and may be formed of G-10 epoxy. The upper sensor coupling plate 151 may have the through-hole through which the SQUID sensor 152 is inserted. The upper sensor coupling plate 151 may include an auxiliary through-hole 1514 through which bubbles of a coolant pass. If the auxiliary through-hole 1514 is formed, vibration caused by the bubbles of the coolant may be suppressed. A trench 1512 may be formed on a bottom surface of the upper sensor coupling plate 151. The trench 1512 may extend to the vicinity of the through-hole 1511. An interconnection from the SQUID sensor 152 may be buried in the trench 1512. A module coupling pillar through-hole 1516 may be formed in the center of the upper sensor coupling plate 151. A coupling tool coupling through-hole 1515 may be formed at the upper sensor coupling plate 151. The SQUID sensor module 150 is mounted on the inner body portion 114 via a coupling tool (not shown) coupled with the coupling tool coupling through-hole 1515. A maximum diameter D3 of the upper sensor coupling plate 151 is smaller than the diameter D1 of the neck portion.

The upper printed circuit board 154 may have a disc shape, and a quadrangular through-hole 1541 may be formed at a position away from the center of the upper printed circuit board 154. The upper printed circuit board 154 may be aligned with the through-hole 1511 of the upper sensor coupling plate 151 to be mounted on a bottom surface of the upper sensor coupling plate 151. The upper printed circuit board 154 may include a connector 1542. The connector 1542 may be electrically connected to the connector 1551 of the SQUID sensor 152.

The lower sensor coupling plate 153 may have a fan shape and may be formed of G-10 epoxy. The lower sensor coupling plate 153 may have the protrusion 1531 disposed to be aligned with the through-hole 1511 of the upper sensor coupling plate 151.

The SQUID sensor module 150 may include a module coupling pillar 157 coupled with the inner bottom plate 115 through a central region of the fan shape. One end 1571 of the module coupling pillar 157 may be in the form of a square pillar, and the other end 1572 thereof may be in the form of a male screw.

The inner bottom plate 115 of the inner container may include a partition 117 to have a fan shape. An outer circumferential surface of the inner bottom plate 115 may protrude such that the lower sensor coupling plate 153 is inserted and aligned with the inner bottom plate 115. The inner bottom plate 115 may include a module coupling pillar coupling nut 116. The module coupling pillar coupling nut 116 may be inserted into a groove formed on the inner bottom plate 115 and fixed using an epoxy resin. The other end of the module coupling pillar 157 may be coupled with the module coupling pillar coupling nut 116 protruding from the through-hole 1532 of the lower sensor coupling plate 153.

A groove is formed at a lower portion of the protrusion 1531 of the lower sensor coupling plate 153, and fixing structure 156 may fix the lower sensor coupling plate 153 and the other end of the SQUID sensor 152 to each other. A coupling nut 1517 may fix one end of the SQUID sensor 152 and the upper sensor coupling plate 151 to each other.

The SQUID sensor 152 may include a bobbin 1521 on which a pick-up coil 1527 is wound, a SQUID 1525 mounted on the bobbin 1521 and electrically connected to the pick-up coil 1527, and a printed circuit board 155 electrically connected to the SQUID 1525 and fixed to the bobbin 1521. The bobbin 1521 may include a cylindrical body portion 1521a, a cut-out portion 1521b which is connected to the body portion 1521a and cut out such that its side surface forms a plane, a square-pillar portion 1521c that is connected to the cut-out portion 1521b and has a square section, and a cylindrical portion 1521d extending from the center of the square-pillar portion 1521c. A groove 1526 is formed on a bottom surface of the body portion 1521a.

The printed circuit board 155 may be removably connected to the SQUID 1525 through a connection pin. The printed circuit board 155 may be mounted on a bottom surface of the square-pillar portion 1521c, and a connector 1551 of the printed circuit board 155 may be removably connected to a connector 1542 of the upper printed circuit board 154.

Each of the SQUID sensor modules 150a to 150d may include a manganin wire 194 electrically connected to the SQUID sensor module, a braided wire 192 to protect the manganin wire 194, and a connection connector 135 connected to the managing wire 194. The connection connector 135 may be inserted into the intermediate connection block 135 to be electrically connected thereto.

A manganin wire protected by a plastic braided wire is used for driving and signal transmission of the SQUID sensor 152. A single SQUID sensor includes eight connection terminals to drive bias current, an output voltage, feedback, and a heater. An interconnection of a single 16-channel SQUID sensor module is connected to four 32-pin connectors through the manganin wire. Thus, the four SQUID sensor modules are connected to the intermediate connection block 135 through sixteen 32-pin connectors 196.

Interconnections of the respective SQUID sensor modules 150a to 150d are gathered into a G-10 epoxy guide tube 1591. Each of the interconnections is connected to the 32-pin connector 196 through the manganin wire 194 protected by the plastic braided wire 192. All the interconnections may be protected by a plastic braided wire with superior flexibility to protect a damage that may occur when the SQUID sensor module is assembled or disassembled from a low-temperature coolant storage container. Electrical connection between the upper connection block 137 and the intermediate connection block 135 may be achieved using a manganin wire with low conductivity.

Each of the SQUID sensor modules 150a to 150d prevented individual vibration and constantly maintained distance between SQUID sensors and their direction by cross-coupling sixteen SQUID sensors.

In order to insert each SQUID sensor module coupled with a SQUID sensor into the inner container, a first coupling tool (not shown) seats each SQUID sensor module on the bottom of a storage container and a second coupling tool (not shown) couples a bolt disposed on the SQUID sensor module with a nut fixed at the bottom of the storage container.

According to the present disclosure, an evaporation of liquid helium was dramatically reduced by decreasing a sectional area of a neck portion of an inner container. Moreover, vibration caused by external vibration and internal helium gas was isolated by mechanically decoupling a baffle of an insert and a sensor coupling plate.

As described above, a cooling apparatus according to the present disclosure decreases an evaporation rate of a coolant in a low-temperature coolant storage container for cooling a SQUID sensor and removes vibration noise transferred through a measurement probe on which the SQUID sensor is mounted. Thus, the SQUID sensor may operate stably and a high signal-to-noise ratio may be achieved.

A cooling apparatus according to the present disclosure was applied to an axial-type 64-chhanel magnetocardiography (MCG) system. A unit SQUID sensor module included sixteen channels, and the MCG system included four modules. A system unstable operation caused by individual vibration of a SQUID sensor coupled with each SQUID sensor module was removed, and vibration noise was removed to improve a signal-to-noise ratio. Moreover, since the shape of a low-temperature coolant storage container may be changed, an evaporation rate of liquid helium was reduced more than 50 percent.

Although the present disclosure has been described in connection with the embodiment of the present disclosure illustrated in the accompanying drawings, it is not limited thereto. It will be apparent to those skilled in the art that various substitutions, modifications and changes may be made without departing from the scope and spirit of the present disclosure.

What is claimed is:

1. A low-temperature cooling apparatus comprising:
   an outer container;
   an inner container disposed inside the outer container, the inner container including a neck portion having a first diameter and a body portion having a second diameter greater than the first diameter;
   an insert inserted into the neck portion of the inner container; and
   a plurality of SQUID sensor modules inserted into the body portion of the inner container
   wherein each of the plurality of SQUID sensor modules is in the form of a circular-sector pillar and is fixedly coupled with an inner bottom plate of the inner container;
   wherein each of the plurality of SQUID sensor modules comprises:
      an upper sensor-coupling plate having a through-hole;
      a lower sensor-coupling plate including a protrusion disposed to be aligned with the through-hole;
      an upper printed circuit board disposed below the upper sensor-coupling plate, the upper printed circuit board having a printed circuit board through-hole aligned with the through-hole; and
      a SQUID sensor;
      wherein one end of each SQUID sensor is inserted into the through-hole and the printed circuit board through-hole; and
      wherein another end of each SQUID sensor has a groove that is disposed on the protrusion of the lower sensor-coupling plate.

2. The low-temperature cooling apparatus as set forth in claim 1, wherein the inner bottom plate includes a partition such that the SQUID sensor module is inserted and aligned with the inner bottom plate.

3. The low-temperature cooling apparatus as set forth in claim 1, wherein the insert further comprises an intermediate connection block, and
   wherein an interconnection of the SQUID sensor module is electrically connected to the intermediate connection block.

4. The low-temperature cooling apparatus as set forth in claim 1, wherein the upper sensor coupling plate further has an auxiliary through-hole.

5. The low-temperature cooling apparatus as set forth in claim 1, wherein the upper sensor coupling plate further has a trench formed on its bottom surface.

6. The low-temperature cooling apparatus as set forth in claim 1, wherein the SQUID sensor module further comprises a module coupling pillar coupled with the inner bottom plate through a fan-shaped central region.

7. The low-temperature cooling apparatus as set forth in claim 1, wherein the SQUID sensor comprises:
   a bobbin on which a pick-up coil is wound;
   a SQUID mounted on the bobbin and electrically connected to the pick-up coil; and
   a printed circuit board electrically connected to the SQUID and fixed to the bobbin.

8. The low-temperature cooling apparatus as set forth in claim 7, wherein the bobbin comprises:
   a cylindrical body portion;
   a cut-out portion connected to the body portion and cut out such that its side surface forms a plane;

a square-pillar portion connected to the cut-out portion, the square-pillar portion having a square section; and a cylindrical portion extending from the center of the square-pillar portion, wherein the groove is formed on a bottom surface of the body portion.

9. The low-temperature cooling apparatus as set forth in claim 1, wherein each of the SQUID sensor modules comprises:

a copper-manganese-nickel alloy wire electrically connected to the SQUID sensor module;

a plastic braided wire to protect the copper-manganese-nickel alloy wire; and a connection connector connected to the copper-manganese-nickel alloy wire.

10. A SQUID sensor module inserted into a low-temperature cooling apparatus including an inner container and an outer container, the SQUID sensor module comprising:

an upper sensor coupling plate having a coupling groove and a through-hole through which a coupling tool is coupled;

a lower sensor coupling plate including a protrusion disposed to be aligned with the through-hole;

an upper printed circuit board disposed below the upper sensor coupling plate, the upper printed circuit board having a printed circuit board through-hole aligned with the through-hole; and a SQUID sensor having one end inserted into the through-hole and the printed circuit board through-hole and the other end having a groove disposed on the protrusion.

11. The SQUID sensor module as set forth in claim 10, wherein the upper sensor coupling plate further has an auxiliary through-hole through which coolant bubbles pass.

12. The SQUID sensor module as set forth in claim 10, wherein the upper sensor coupling plate further has a trench formed on its bottom surface, and wherein interconnections of the SQUID sensor module are buried in the trench.

13. The SQUID sensor module as set forth in claim 10, further comprising:

a module coupling pillar coupled with a bottom plate of the inner container through the SQUID sensor module.

14. The SQUID sensor module as set forth in claim 10, wherein the SQUID sensor comprises:

a bobbin on which a pick-up coil is wound;

a SQUID mounted on the bobbin and electrically connected to the pick-up coil; and a printed circuit board electrically connected to the SQUID and fixed to the bobbin.

15. The SQUID sensor module as set forth in claim 14, wherein the bobbin comprises:

a cylindrical body portion;

a cut-out portion connected to the body portion and cut out such that its side surface forms a plane;

a square-pillar portion connected to the cut-out portion, the square-pillar portion having a square section; and a cylindrical portion extending from the center of the square-pillar portion, wherein the groove is formed on a bottom surface of the body portion.

16. The SQUID sensor module as set forth in claim 10, wherein the SQUID sensor module further comprises:

a copper-manganese-nickel alloy wire electrically connected to the SQUID sensor module;

a plastic braided wire to protect the copper-manganese-nickel alloy wire; and a connection connector connected to the copper-manganese-nickel alloy wire.

* * * * *